United States Patent [19]

Christensen et al.

[11] 4,310,538
[45] Jan. 12, 1982

[54] 3-HALO-1-AZABICYCLO[3.2.0]HEPT-2-EN-7-ONE-2-CARBOXYLIC ACID

[75] Inventors: Burton G. Christensen, Scotch Plains; Ronald W. Ratcliffe, Matawan, both of N.J.

[73] Assignee: Merck & Co., Inc., Rahway, N.J.

[21] Appl. No.: 152,913

[22] Filed: May 23, 1980

Related U.S. Application Data

[63] Continuation-in-part of Ser. No. 26,979, Apr. 4, 1979, abandoned, which is a continuation of Ser. No. 843,374, Oct. 19, 1974, abandoned.

[51] Int. Cl.³ .................. C07D 487/04; A61K 31/40; C07D 705/08
[52] U.S. Cl. ..................... 424/274; 260/245.2 T; 260/239 A
[58] Field of Search .............. 260/245.2 T; 424/274

[56] References Cited

U.S. PATENT DOCUMENTS 3,567,732 3/1971 Foly et al. ..................... 546/153

3,697,515 10/1972 Fechtig ........................ 544/19

*Primary Examiner*—Mark L. Berch
*Attorney, Agent, or Firm*—James A. Arno; Hesna J. Pfeiffer

[57] ABSTRACT

Disclosed is 3-halo-1-azabicyclo[3.2.0]hept-2-en-7-one-2-carboxylic acid (I):

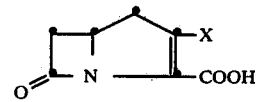

I

Such compounds, wherein X is halo, and their pharmaceutically acceptable salt, ester and amide derivatives are useful as antibiotics. Also disclosed are processes for the preparation of such compounds, pharmaceutical compositions comprising such compounds and methods of treatment comprising administering such compounds and compositions when an antibiotic effect is indicated.

2 Claims, No Drawings

3-HALO-1-AZABICYCLO[3.2.0]HEPT-2-EN-7-ONE-2-CARBOXYLIC ACID

This application is a continuation-in-part of U.S. patent application Ser. No. 026,979 filed Apr. 4, 1979 now abandoned which is a continuation of U.S. patent application Ser. No. 843,374 filed Oct. 19, 1977, now abandoned.

BACKGROUND OF THE INVENTION

This invention relates to the antibiotic 3-halo-1azabicyclo[3.2.0]hept-2-ene-7-one-2-carboxylic acid (I) and to its pharmaceutically acceptable salt, ester and amide derivatives:

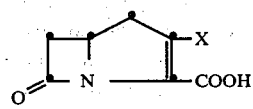

wherein X is halo, such as chloro or bromo.

The compounds of the present invention (I) are also useful as intermediates in the preparation of the 6-(1'-hydroethyl)-3-substituted-1-azabicyclo[3.2.0]hept-2-en-7-one-2-carboxylic acids which are also antibiotics; such compounds are disclosed in commonly assigned U.S. patent application Ser. No. 000,470 filed Jan. 2, 1979 which is a continuation of U.S. patent apolication Ser. No. 843,620 filed Oct. 19, 1977, now abandoned, which application is incorporated herein by reference.

This invention also relates to processes for the preparation of such compounds (I); pharmaceutical compositions comprising such compounds; and to methods of treatment comprising administering such compounds and compositions when an antibiotic effect is indicated.

There is a continuing need for new antibiotics. For unfortunately, there is no static effectiveness of any given antibiotic because continued wide scale usage selectively gives rise to resistant strains of pathogens. In addition, the known antibiotics suffer from the disadvantage of being effective only against certain types of microorganisms. Accordingly the search for new antibiotics continues.

Thus, it is an object of the present invention to provide a novel class of antibiotics and intermediates to antibiotics which are useful in animal and human therapy and in inanimate systems. These antibiotics are active against a broad range of pathogens which representatively include both gram positive bacteria such as *S. aureus, Strep. pyogenes* and *B. subtilis*, and gram negative bacteria such as *E. coli, Proteus morganii, Pseudomonas, Serratia* and *Klebsiella*. Further objects of this invention are to provide chemical processes for the preparation of such antibiotics and their non-toxic pharmaceutically acceptable salts; pharmaceutical compositions comprising such antibiotics; and to provide methods of treatment comprising administering such antibiotics and compositions when an antibiotic effect is indicated.

DETAILED DESCRIPTION OF THE INVENTION

The preparation of the compounds (I) of the present invention may conveniently be summarized by the following reaction diagram:

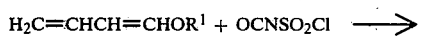

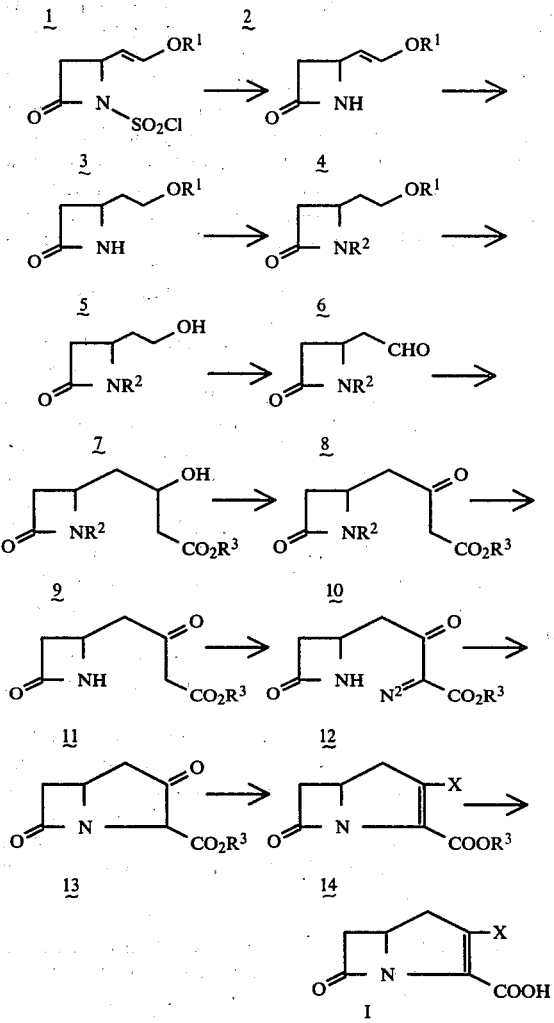

In words relative to the above reaction diagram starting material 4 and 8 and the reaction sequence 1→→8 are disclosed in co-pending, commonly assigned U.S. patent application Ser. No. 792,071 filed April 28, 1977; this application, as it relates to these starting materials, is incorporated herein by reference. Basically, however, the 4-(2-substituted-vinyl)azetidine-2-one, 4 starting material is prepared by reacting an $R^1$-oxybutadiene, 1, with chlorosulfonylisocyanate 2. The reaction is conducted without solvent or may be run in solvent such as diethyl ether, ethyl acetate, chloroform, methylene chloride, or the like, at a temperature of from −78° C. to 25° C. for from a few minutes to 1 hour to provide 3. The radical $R^1$ is an easily removable acyl blocking group such as an alkanoyl or aralkanoyl which bears no functional group or groups which might interfere with the desired course of reaction (1+2→3→4). Intermediate species 3 is converted to the sulfinamide by reduction which is then hydrolyzed to 4 at pH 6–8. Typically the reaction solution comprising 3 is contacted (5–30 minutes) with an aqueous solution (at 0°–25° C.) of a reducing agent such as sodium sulfite, thiophenol, or the like, at pH 6–8 to provide 4.

The reaction 4→5 is a reduction, and is preferably achieved by hydrogenation in a solvent such as ethyl acetate, ether, dioxane, tetrahydrofuran(THF), ethanol or the like at 0° to 25° C. for from 5 minutes to 2 hours under 1 to 10 atmospheres of hydrogen in the presence of a hydrogenation catalyst such as a platinum metal or oxide thereof such as 10% Pd/C or the like.

The reaction 5→7 establishes, if desired, the N-protecting group $R^2$, which preferably is a cyclic ether such as 2-tetrahydropyranyl or a triorganosilyl radical, such as trimethylsilyl or t-butyl-dimethylsilyl. Alternatively, $R^2$ may be hydrogen. Typically, when the protecting group $R^2$ is a triorganosilyl radical, such as t-butyldimethylsilyl, species 5 in a solvent such as DMF, dioxane, THF, $Et_2O$ or the like in the presence of a base such as triethylamine, imidazole, pyridine, hexamethyldisilazane or the like is contacted with the desired silylating agent such as t-butyldimethylsilylchloride, trimethylsilylchloride, isopropyldimethylsilylchloride or the like at a temperature of from −10° to 40° for from 10 mins to 8 hours. Suitable reagents for the establishment of $R^2$ when $R^2$ is a cyclic ether such as 2-tetrahydropyranyl, 2-methoxy-2-tetrahydropyranyl, 4-methoxy-4-tetrahydropyranyl or the like are: 2,3-dihydro-4H-pyran, 6-methoxy-2,3-dihydro-4H-pyran, 4-methoxy-5,6-dihydro-2H-pyran and the like. The establishment of such cyclic ether protecting groups is typically conducted in a solvent such as $Et_2OAc$, EtOAc, dioxane, DMF and the like in the presence of an acid, HCl, toluenesulfonic acid, or phosphoryl chloride at a temperature of from 0° to 25° C. for from 10 min to 3 hrs.

The deblocking reaction 6→7 is preferably accomplished by alcoholysis wherein the solvent is a loweralkanol such as methanol, ethanol or the like in the presence of the corresponding alkali metal alkoxide, such as sodium methoxide. Typically, the reaction is conducted for from 5 minutes to 3 hours at a temperature of from −10° to 25° C.

The aldehyde intermediate 8 is prepared by treating 7 with an oxidizing agent such as $CrO_3.2$(pyridine) in $CH_2Cl_2$, 1:1 mixture of dimethylsulfoxide (DMSO) and acetic anhydride, pyridinium chlorochromate in $CH_2Cl_2$, dicyclohexylcarbodiimide in DMSO, or the like at a temperature of from 0°-25° C. for from 5 minutes to 8 hours.

The condensation of the aldehyde to provide species 9 (8→9), is accomplished by treating 8 in a solvent such as $Et_2O$, (diethylether), THF (tetrahydrofuran), HMPA (hexamethylphosphoramide), DMF(dimethylphosphoramide) or the like at a temperature of from −78° to 0° C. for from 1 min to 1 hour in the presence of a base such as lithium diisopropylamide, KH, or the like with an ester of acetic acid ($CH_3CO_2R^3$; wherein $R^3$ is a readily removable carboxyl protecting group or a pharmaceutically acceptable ester moiety; suitable values for $R^3$ are defined below).

Intermediate ketone species 10 is obtained by oxidation of 9 following the previously described oxidation procedure 7→8. The N-protecting group $R^2$ is easily removed by mild acid hydrolysis such as acetic acid in water at a temperature of from 25° to 100° C. for from 1 to 20 hours to provide species 11 (10→11).

The diazo species 12 is prepared from 11 by treating 11 in a solvent such as $CH_3CN$, $CH_2Cl_2$, THF and the like with an azide such as p-carboxy benzenesulfonylazide, toluenesulfonylazide, methanesulfonylazide and the like in the presence of base such as triethylamine, pyridine, $(C_2H_5)_2NH$ and the like for from 1 to 50 hours at 0° to 25° C.

Cyclization of the diazo compound to provide 13(12→13) is preferably accomplished by irradiating through a pyrex filter (λ greater than 300 nm) in a solvent such as benzene, $CCl_4$, $Et_2O$, or the like at a temperature of from 0° to 25° C. for from 0.5 to 2 hours. Alternatively, cyclization of the diazo compound is accomplished by heating in a solvent such as benzene (φH), toluene (φMe), THF or the like at a temperature of from 50° to 110° C. for from 1–5 hrs in the presence of a catalyst such as bis (acetylacetonato)Cu (II) [Cu(acac)$_2$], $CuSO_4$, Cu powder, Rh(OAc)$_2$, or Pd(OAc)$_2$. Species 13 may also be prepared according to the disclosure found in European patent application No. 79101307.1 (filed May 1, 1979), publication 007973/Al, which is incorporated herein by reference, when the procedure disclosed omits the alkylation schemes which establish the hydroxyethyl moiety, step 7→8.

The 3-keto intermediate 13 is converted to the 3-halo species by treating 13 with a halogenating agent such as $PCl_3$, $SOCl_2$, $POCl_3$, $(COCl)_2$, $PBr_3$, $SOBr_2$ or the like in a solvent such as DMF, $CHCl_3$, φH or the like for from 0.5 to 8 hours at 0° to 80° C. Preferred reagents and conditions for preparation of the 3-chloro species are $PCl_3$ or $SOCl_2$ in a solvent such as DMF, at a temperature of 0° to 25° C. for from 1 to 6 hours. Preferred reagents and conditions for preparation of the 3-bromo species are $PBr_3$ or $SOBr_2$ in a solvent such as DMF, at a temperature of from 0° to 25° C. for from 1 to 6 hours. Species 14 may be deblocked if desired to provide I by mild aqueous hydrolysis or hydrogenolysis.

The compounds of the present invention may also generically be represented by the following structural formula:

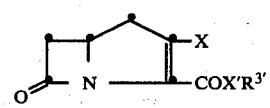

Ia wherein X′ is oxygen, sulfur or NR′ (R′ is hydrogen or loweralkyl having from 1 to 6 carbon atoms); and $R^{3'}$ is representatively selected to provide the pharmaceutically acceptable salt, ester, anhydride ($R^{3'}$ is acyl) and amide moieties known in the bicyclic β-lactam antibiotic art.

Identification of the Radical —COX′R$^{3'}$

In the generic representation of the compounds of the present invention (Ia, above), the radical represented by —COX′R$^{3'}$ is, inter alia, —COOH (X′ is oxygen and $R^{3'}$ is hydrogen) and all radicals known to be effective as pharmaceutically acceptable ester, anhydride ($R^{3'}$ is acyl) and amide radicals in the bicyclic β-lactam antibiotic art, such as the cephalosporins and penicillins and the nuclear analogues thereof.

Suitable radicals ($R^{3'}$) include conventional protecting or carboxyl blocking groups. The term "blocking group" as utilized herein is employed in the same manner and in accordance with the teaching of U.S. Pat. No. 3,697,515 which is incorporated herein by reference. Suitable blocking esters thus include those selected from the following list which is represetative and not intended to be an exhaustive list of possible ester groups, wherein X′=O and $R^{3'}$ is given:

(i) $R^{3'}=CR^aR^bR^c$ wherein at least one or $R^a$, $R^b$ and $R^c$ is an electron-donor, e.g., p-methoxyphenyl, 2,4,6-tri-methylphenyl, 9-anthryl, methoxy, $CH_2SCH_3$, tetrahydrofur-2-yl, tetrahydropyran-2-yl or fur-2-yl. The remaining $R^a$, $R^b$ and $R^c$ groups may be hydrogen or organic substituting groups. Suitable ester groups of this type include p-methoxybenzyloxycarbonyl and 2,4,6-trimethylbenzyloxycarbonyl.

(ii) $R^{3'}=CR^aR^bR^c$ wherein at least one of $R^a$, $R^b$ and $R^c$ is an electron-attracting group, e.g., benzoyl, p-nitrophenyl, 4-pyridyl, trichloromethyl, tribromomethyl, iodomethyl, cyanomethyl, ethoxycarbonylmethyl, arylsulphonylmethyl, 2-dimethylsulphoniummethyl, o-nitrophenyl or cyano. Suitable esters of this type include benzoylmethoxycarbonyl, p-nitrobenzyloxycarbonyl, 4-pyridylmethoxycarbonyl, 2,2,2-trichloroethoxycarbonyl and 2,2,2-tribromoethoxycarbonyl.

(iii) $R^{3'}CR^aR^bR^c$ wherein at least two of $R^a$, $R^b$ and $R^c$ are hydrocarbon such as alkyl, e.g., methyl or ethyl, or aryl, e.g., phenyl and the remaining $R^a$, $R^b$ and $R^c$ group, if there is one, is hydrogen. Suitable esters of this type include t-butyloxycarbonyl, t-amyloxycarbonyl, diphenylmethoxycarbonyl and triphenylmethoxycarbonyl.

(iv) $—R^{3'}=R^d$, wherein $R^d$ is adamantyl, 2-benzyloxyphenyl, 4-methylthiophenyl or tetrahydropyran-2-yl.

Silyl esters, under this category of blocking groups, may conveniently be prepared from a halosilane or a silazane of the formula:

$R^4_3SiX'$; $R^4_2SiX'_2$; $R^4_3Si.NR^4_2$; $R^4_3Si.NH.COR^4$; $R^4_3Si.NH.CO.NH.SiR^4_3$; $R^4NH.CO.NH^4.SiR^4_3$; or $R^4C(OSiR^4_3)$; $HN(SiR^4_3)_2$ wherein $X'$ is a halogen such as chloro or bromo and the various groups $R^4$, which can be the same or different, represent hydrogen atoms or alkyl, e.g., methyl, ethyl, n-propyl, iso-propyl; aryl, e.g., phenyl; or aralkyl, e.g., benzyl groups.

More generally stated, pharmaceutically acceptable carboxyl derivatives of the present invention are those derived by reacting I with alcohols, phenols, mercaptans, thiophenols, acylating reagents and the like. For example, esters and amides of interest are the above-listed starting materials and final products having the following group at the 2-position of the nucleus: —COX'R$^{3'}$ wherein X' is oxygen, sulfur, or NR' (R' is H or R$^{3'}$) and R$^{3'}$ is alkyl having 1-10 carbon atoms, straight or branched, such as methyl, ethyl, t-butyl, pentyl, decyl and the like; carbonylmethyl, including phenacyl, p-bromophenacyl, p-t-butylphenacyl, acetoxyacetylmethyl, pivaloxyacetylmethyl, carboxymethyl, and its alkyl and aryl esters, α-carboxy-α-isopropyl; aminoalkyl including 2-methylaminoethyl, 2-diethylaminoethyl, 2-acetamidoethyl, phthalimidomethyl, succinimidomethyl; alkoxyalkyl wherein the alkoxy portion has 1-10 and preferably 1-6 carbon atoms; but can be branched, straight or cyclic, and the alkyl portion has 1-6 carbon atoms, such as methoxymethyl, ethoxymethyl, isopropoxymethyl, decyloxymethyl, ethoxypropyl, decyloxypentyl, cyclohexyloxymethyl and the like; alkanoyloxyalkyl wherein the alkanoyloxy portion is straight or branched and has 1-6 carbon atoms and the alkyl portion has 16 carbon atoms, such as acetoxymethyl, pivaloyloxymethyl, acetoxyethyl, propionyloxyethyl, acetoxypropyl, and the like; haloalkyl wherein halo is chloro, bromo, fluoro, or iodo, and the alkyl portion is straight or branched having 1-6 carbon atoms, e.g., 2,2,2-trichloroethyl, trifluoroethyl, 2-bromopropyl, diiodomethyl, 2-chloroethyl, 2-bromoethyl, and the like; alkenyl having 1-10 carbon atoms, either straight or branched, e.g., allyl, 2-propenyl, 3-butenyl, 4-butenyl, 4-pentenyl, 2-butenyl, 3-pentenyl, 3-methyl-3-butenyl, metallyl, 1,4-cyclohexadien-1-ylmethyl, and the like alkynyl having 1-10 carbon atoms, either straight or branched e.g., 3-pentenyl, propargyl, ethynyl, 3-butyn-1-yl, and the like; alkanoyl, either straight or branched, having 1-10 carbon atoms, such as pivaloyl, acetyl, propionyl, and the like; aralkyl or heteroaralkyl wherein alkyl has 1-3 carbon atoms, and hetero means 1-4 hetero atoms being selected from the group consisting of O, S, or N, such as benzyl, benzhydryl, and substituted benzyl, benzhydryl, or e.g., benzyl or benzhydryl substituted with 1-3 substituents such as benzyl, phenoxy, halo, loweralkyl, loweralkanoyloxy of 1-5 carbon atoms, lower alkoxy, hydroxy, nitro, blocked carboxy, or combinations thereof, e.g., p-chlorobenzyl, o-nitrobenzyl, 3,5-dinitrobenzyl, p-methoxybenzyl, m-benzoylbenzyl, p-t-butylphenyl, m-phenoxybenzyl, p-benzoylbenzyl, p-nitrobenzyl, 3,5-dichloro-4-hydroxybenzyl, p-methoxycarbonylbenzyl, p-methoxybenzhydryl, p-carboxybenzyl, the latter being either the free acid, ester or the sodium salt, 2,4,6-trimethylbenzyl, p-pivaloyloxybenzyl, p-t-butoxycarbonyl benzyl, p-methylbenzyl, p-benzoyloxybenzyl, p-acetoxybenzyl, p-2-ethylhexanoylbenzyl, p-ethoxycarbonylbenzyl, p-benzoylthiobenzyl, p-benzamidobenzyl, o-pivaloyloxybenzyl, m-pivaloyloxybenzyl, p-isopropoxybenzyl, p-t-butoxybenzyl, as well as the cyclic analogues thereof, 2,2-dimethyl-5-coumaranmethyl, 5-indanylmethyl, p-trimethylsilylbenzyl, 3,5-bis-t-butoxy-4-hydroxybenzyl; 2-thienylmethyl, 2-furylmethyl, 3-t-butyl-5-isothiazolmethyl, 6-pivaloyloxy-3-pyridazinylethyl, 5-phenylthio-1-tetrazolylmethyl, or the like (the use of the terms lower alkyl or lower alkoxy in this context means 1-4 carbon atoms chain); or phthalidyl; or phenylethyl, 2-(p-methylphenyl)ethyl, and the arylthioalkyl analogues, aryloxyalkyl wherein aryl is preferably a phenyl ring having 0-3 substituents preferably 0 or 1 substituents in the ortho or para positions and alkyl is 1-6 carbon atoms, e.g., (4-methoxy)-phenoxymethyl, phenoxymethyl, (4-chloro)phenoxymethyl, (4-nitro)phenoxymethyl, (4-benzyloxy)-phenoxymethyl, (4-methyl)phenoxymethyl, (4-benzyloxy)phenoxymethyl, (4-methyl)phenoxymethyl, (2-methoxy)phenoxymethyl, (1-phenoxy)ethyl, (4-amino)-phenoxymethyl, (4-methoxy)phenylthiomethyl, (4-chloro)phenylthiomethyl, phenylthioethyl; aryl wherein aryl is phenyl, 5-indanyl, or substituted phenyl having 0-3 substituents, preferably 0 or 1 substituent in the ortho or para position, e.g., (4-methyl)phenyl, (4-hydroxy)phenyl, (4-t-butyl)phenyl, p-nitrophenyl, 3,5-dinitrophenyl, or p-carboxyphenyl, the latter having either the free acid or the sodium salt form; aralkenyl wherein aryl is phenyl and alkenyl has 1-6 carbon atoms, such as 3phenyl-2-propenyl; aralkoxyalkyl wherein aralkoxy is benzyloxy, and alkyl has 1-3 carbon atoms, such as benzyloxymethyl, (4-nitro)benzyloxymethyl, (4-chloro)benzyloxymethyl; alkylthioalkyl wherein the alkylthio portion has 1-10 and preferably 1-6 carbon atoms, but can be branched, straight or cyclic, and the alkyl portion has 1-6 carbon atoms, such as methylthioethyl, ethylthioethyl, cyclohexylthiomethyl, decylthiobutyl, methylthiopropyl, isopropylthioethyl, methylthiobutyl and the like.

In addition to the esters (and thio esters) listed above, amides are also embraced by the present invention, i.e., wherein X' is the

group. Representative of such amides are those wherein R' is selected from the group consisting of hydrogen, methyl, ethyl, phenyl, p-methoxyphenyl, benzyl, carboxymethyl, methylthioethyl, and heteroaryl; also embraced by —COX'R$^{3'}$ are anhydrides wherein R$^{3'}$ is acyl, for example, benzyloxycarbonyl, ethoxycarbonyl, benzoyl, and pivaloyl.

The most preferred —COX'R$^{3'}$ radicals of the present invention are those wherein (relative to Structure Ia above X' is oxygen, sulphur or NR' (R' is selected from the group consisting of hydrogen and lower alkyl); and R$^{3'}$ is selected from the group consisting of: loweralkyl, lower alkenyl, such as methallyl, 3-methylbutenyl, 3-butenyl, and the like; methylthioethyl; benzyl and substituted benzyl such as p-t-butylbenzyl, m-phenoxybenzyl, p-pivaloyloxybenzyl, p-nitrobenzyl and the like; pivaloyloxymethyl, 3-phthalidyl and acetoxymethyl, propionyloxymethyl, acetylthiomethyl, pivaloylthiomethyl, allyl, 4-butenyl, 2-butenyl, 3-methyl-2-butenyl, phenacyl, acetoxyacetylmethyl, methoxymethyl, p-acetoxybenzyl, p-pivaloyloxybenzyl, p-isopropoxybenzyl, 5-indanylmethyl, 5-indanyl, benzyloxymethyl, ethylthioethyl, methylthiopropyl, methoxycarbonyloxymethyl, ethoxycarbonyloxymethyl, dimethylaminoacetoxymethyl, crotonolacton-3-yl, and acetamidomethyl.

The preferred carboxylic salts of I are: alkali and alkaline metal salts such as sodium, potassium, and calcium salts; amine salts such as benzhydrylamine, N-benzyl-2-phenethylamine, N,N'-dibenzylethylenediamine, and procaine salts.

The salts of this invention are pharmacologically acceptable non-toxic derivatives which can be used as the active ingredient in suitable unit dosage pharmaceutical forms. Also, they may be combined with other drugs to provide compositions having a broad spectrum of activity.

The novel compounds are valuable antibiotics active against various gram-positive and gram-negative bacteria and, accordingly, find utility in human and veterinary medicine. The compounds of this invention can therefore be used as antibacterial drugs for treating infections caused by gram-positive or gram-negative bacteria, for example, against *Staphylococcus aureus, Escherichia coli, Klebsiella pneumoniae, Serratia, Salmonella typhosa, Pseudomonas* and *Bacterium proteus*. The antibacterials of the invention may further be utilized as additives to animal feeding stuffs, for preserving foodstuffs and as disinfectants. For example, they may be employed in aqueous compositions in concentrations ranging from 0.1 to 100 parts of antibiotic per million parts of solution in order to destroy and inhibit the growth of harmful bacteria on medical and dental equipment and as bactericides in industrial applications, for example, in waterbased paints and in the white water of paper mills to inhibit the growth of harmful bacteria.

The products of this invention may be used alone or in combination as an active ingredient in any one of a variety of pharmaceutical preparations. These antibiotics and their corresponding salts may be employed in capsule form or as tablets, powders or liquid solutions or as suspensions or elixirs. They may be administered orally, intravenously or intramuscularly.

The compositions are preferably presented in a form suitable for absorption by the gastro-intestinal tract. Tablets and capsules for oral administration may be in unit dose presentation form, and may contain conventional excipients such as binding agents, for example, syrup, acacia, gelatin, sorbitol, tragacanth, or polyvinylpyrrolidone; fillers for example, lactose, sugar, maizestarch, calcium phosphate, sorbitol or glycine; lubricants, for example, magnesium stearate, talc, polyethylene glycol, silica; disintegrants, for example, potato starch or acceptable wetting agents such as sodium lauryl sulphate. The tablets may be coated according to methods well known in the art. Oral liquid preparations may be in the form of aqueous or oily suspension, solution, emulsions, syrups, elixirs, etc. or may be presented as a dry product, for reconstitution with water or other suitable vehicles before use. Such liquid preparations may contain conventional additives such as suspending agents, for example, sorbitol syrup, methyl cellulose, glucose/sugar syrup, gelatin, hydroxyethylcellulose, carboxymethyl cellulose, aluminum stearate gel or hydrogenated edible oils, for example almond oil, fractionated coconut oil, oily esters, propylene glycol, or ethyl alcohol; preservatives, for example methyl or propyl p-hydroxybenzoates or sorbic acid. Suppositories will contain conventional suppository bases, e.g. cocoa butter or other glyceride.

Compositions for injection may be presented in unit dose form in ampules, or in multidose containers with an added preservative. The compositions may taken such forms as suspensions, solutions, or emulsions in oily or aqueous vehicles, and may contain formulatory agents such as suspending, stabilizing and/or dispersing agents. Alternatively, the active ingredient may be in powder form for reconstitution with a suitable vehicle, e.g. sterile, pyrogen-free water, before use.

The compositions may also be prepared in suitable forms for absorption through the mucous membranes of the nose and throat or bronchial tissues and may conveniently take the form of powder or liquid sprays or inhalants, lozenges, throat paints, etc. For medication of the eyes or ears, the preparations may be presented as individual capsules, in liquid or semi-solid form, or may be used as drops etc. Topical applications may be formulated in hydrophobic or hydrophilic bases as ointments, creams, lotions, paints, powders, etc.

Also, in addition to a carrier, the instant compositions may include other ingredients such as stabilizers, binders, antioxidants, preservatives, lubricators, suspending agents, viscosity agents or flavoring agents and the like. In addition, there may also be included in the composition other active ingredients to provide a broader spectrum of antibiotic activity.

For veterinary medicine the composition may, for example, be formulated as an intramammary preparation in either long or quick-release bases.

The dosage to be administered depends to a large extent upon the condition of the subject being treated and the weight of the host, the route and frequency of administration, the parenteral route being preferred for generalized infections and the oral route for intestinal infections. In general, a daily oral dosage consists of from about 2 to about 600 mg. of active ingredient per kg. of body weight of the subject in one or more applications per day. A preferred daily dosage for adult humans lies in the range of from about 15 to 150 mg. of active ingredient per kg. of body weight.

EXAMPLE 1

Preparation of 4-(2-Acetoxyethyl)-azetidin-2-one

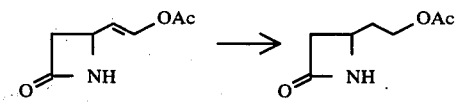

A mixture of 4-(2-acetoxyvinyl)-azetidin-2-one (3.00 g), 10% Pd/C (0.15 g) and ethylacetate (EtOAc) (120 ml) is hydrogenated in a 500 ml glass bomb on a Parr shaker at an initial pressure of 39 psi. After shaking 10 mins (final pressure of 20 psi), the mixture is filtered through a pad of MgSO$_4$ to remove the catalyst. The filtrate is concentrated in vacuo and the residue stripped with anhydrous benzene to provide 4-(2-acetoxyethyl)-azetidin-2-one (3.098 g) as a clear oil: ir (neat) 3.01, 5.66, 5.75, 7.28, 8.05, and 9.61 cm$^{-1}$; nmr (CDCl$_3$) $\delta$1.95 (m, 2), 2.07 (s, 3), 2.60 (m, 1), 3.12 (m, 1), 3.70 (m, 1), 4.15 (m, 2), and 6.77 (br s, 1).

EXAMPLE 2

Preparation of N-(t-Butyldimethylsilyl)-4-(2-acetoxyethyl)-azetidin-2-one

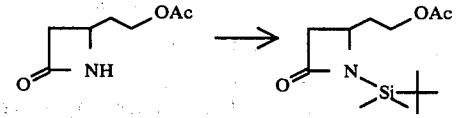

Triethylamine (Et$_3$N) (2.96 ml, 21.2 mmol) and t-butyldimethylsilyl chloride (3.059 g, 20.3 mmol) are added to an ice-cold stirring solution of 4-(2-acetoxyethyl)-azetidin-2-one (3.098 g, 19.3 mmol) in anhydrous dimethylformamide (DMF) (20 ml). A white precipitate appears immediately. The cooling bath is removed and the mixture is stirred at 25° C. (room temperature) for 5 mins. The mixture is diluted with benzene (200 ml), washed with H$_2$O (5×80 ml) and brine, dired with MgSO$_4$, filtered, and evaporated under reduced pressure to afford N-(t-butyldimethylsilyl)-4-(2-acetoxyethyl)-azetidin-2-one (5.078 g) as an off white solid: ir(neat) 5.75, 8.08, 8.41, 11.92, and 12.18 cm$^{-1}$; nmr (CDCl$_3$) $\delta$0.25 (s, 6), 0.98 (s, 9), 1.97 (m, 2), 2.05 (s, 3), 2.67 (dd, 1), 3.20 (dd, 1), 3.62 (m, 1), and 4.12 (t, 2); mass spectrum m/e 214 (M$^+$-57) and 172.

EXAMPLE 3

Preparation of N-(t-Butyldimethylsilyl)-4-(2-hydroxyethyl)-azetidin-2-one

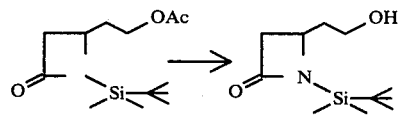

A solution of N-(t-butyldimethylsilyl)-4-(2-acetoxyethyl)-azetidin-2-one (41.7 g, 0.154 mol) in anhydrous methanol (415 ml) is stirred under a N$_2$ atmosphere with ice-bath cooling. A solution of sodium methoxide (415 mg, 7.7 mmol) in anhydrous methanol (15 ml) is added and the resulting solution is stirred in the cold for 2 more hrs. Acetic acid (2.2 ml) is then added and the solvents are evaporated in vacuo (i.v.). The residue is taken up in EtOAc (300 ml), washed with H$_2$O (4×75 ml), 5% NaHCO$_3$ (75 ml) and brine, dried with MgSO$_4$ and evaporated i.v. to a clear oil (21.3 g). This material is purified by chromatography on a Baker silica gel column (425 g, packed under EtOAc). After a 100 ml forefraction, 25 ml EtOAc fractions are collected every 2.5 mins. Fractions 41-49 yield starting material and fractions 51-90 afford N-(t-butyldimethylsilyl)-4-(2-hydroxyethyl)-azetidin-2-one (19.4 g) as a clear oil: ir (neat) 2.88, 5.73, 5.80, 7.52, 7.67, 7.99, 8.40, 11.95, and 12.18 cm$^{-1}$; nmr (CDCl$_3$) $\delta$0.25 (s, 6), 0.98 (s, 9), 1.82 (m, 2), 2.67 (dd, 1), 3.17 (dd, 1), 3.67 (t, 2), and 3.67 (m, 1); mass spectrum m/e 172.

EXAMPLE 4

Preparation of N-(t-Butyldimethylsilyl)-4-(2-oxoethyl)-azetidin-2-one

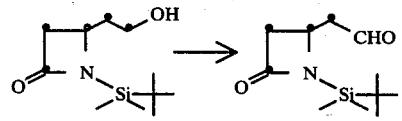

Anhydrous chromium trioxide (CrO$_3$) (1.94 g, 19.4 mmol) is added to a solution of anhydrous pyridine (3.07 g, 38.8 mmole) in anhydrous methylene chloride (CH$_2$Cl$_2$) (50 ml). The resulting mixture is stirred at room temperature for 15 mins. A solution of N-(t-butyldimethylsilyl)-4-(2-hydroxyethyl)-azetidin-2-one (0.74 g, 3.23 mmol) in anhydrous CH$_2$Cl$_2$ (5 ml) is added all at once. After stirring at room temperature for 5 mins, the mixture is decanted and the dark, gummy residue is washed with more CH$_2$Cl$_2$. The combined CH$_2$Cl$_2$ supernatant is evaporated i.v. The residue is tabken up in diethyl ether and filtered to remove chromium salts. The ethereal filtrate is washed with 5% NaHCO$_3$, 5% HCl, 5% NaHCO$_3$ and brine, dried with MgSO$_4$, filtered, and evaporated i.v. to yield N-(t-butyldimethylsilyl)-4-(2-oxoethyl)-azetidin-2-one (0.54 g) as an off-white solid: ir(CHCl$_3$) 5.77, 5.80, 7.36, 7.60, 7.99, 8.50 and 11.95 cm$^{-1}$; nmr (CDCl$_3$) $\delta$0.23(s, 3), 0.27 (s, 3), 0.98 (s, 9), 2.63 (ddd, 1), 2.65 (dd, 1), 3.07 (ddd, 1), 3.37 (dd), 3.97 (m, 1), and 9.78 (t, 1); mass spectrum m/e 170 and 128.

---

The instant compositions may be administered in several unit dosage forms as, for example, in solid or liquid orally ingestible dosage form. The compositions per unit dosage, whether liquid or solid may contain from 0.1% to 99% of active material, the preferred range being from about 10–60%. The composition will generally contain from about 15 mg. to about 1500 mg. of the active ingredient; however, in general, it is preferable to employ a dosage amount in the range of from about 100 mg. to 1000 mg. In parenteral administration the unit dosage is usually the pure compound in a slightly acidified sterile water solution or in the form of a soluble powder intended for solution.

The following Examples, illustrate but do not limit the product, process, compositional or method of treatment aspects of the present invention. All temperatures are given in °C.

EXAMPLE 5

Preparation of
N-(t-Butyldimethylsilyl)-4-(3-benzyloxycarbonyl-2-hydroxypropyl)-azetidin-2-one

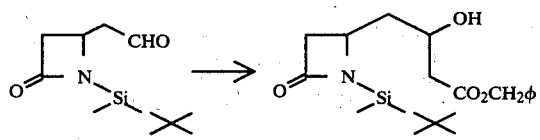

To a flame dried, 50 ml, 3-neck flask fitted with a N₂ inlet, magnetic stirrer, addition funnel, and serum cap are added anhydrous tetrahydrofuran (THF) (10.5 ml) and diisopropyl amine (0.579 ml, 4.13 mmol). The solution is cooled in an ice-methanol bath under N₂ and treated with 2.4 N n-butyl lithium in hexane (1.72 ml). After being stirred at −10° for 15 mins, the solution is cooled to −78° and treated dropwise over 9 mins with a solution of benzyl acetate (0.620 g, 4.13 mmol) in anhydrous THF (3.5 ml). After stirring 15 more mins at −78° C., the reaction mixture is treated dropwise over 13 mins with a solution of N-(t-butyldimethylsilyl)-4-(2-oxoethyl)-azetidin-2-one (0.894 g, 3.93 mmol) in anhydrous THF (6 ml). The reaction mixture is stirred at −78° an additional 15 mins and then quenched with 2.5 N HCl (6 ml). EtOAc (100 ml) is added and the oragnic phase is separated, washed with H₂O (2×20 ml), 5% NaHCO₃ (20 ml) and brine, dried with MgSO₄, and filtered. The filtrate is evaporated i.v. and the residue stripped with φH to yield N-(t-butyldimethylsilyl)-4-(3-benzyloxycarbonyl-2-hydroxypropyl)-azetidin-2-one (1.432 g) as an oil: ir (neat) 2.87, 5.73, 7.57, 7.96, 8.39, 11.92, and 12.16 cm⁻¹; mass spectrum m/e 362, 320, 278, 170 and 128.

EXAMPLE 6

Preparation of
N-(t-Butyldimethylsilyl)-4-(3-benzyloxycarbonyl-2-oxopropyl)-azetidin-2-one

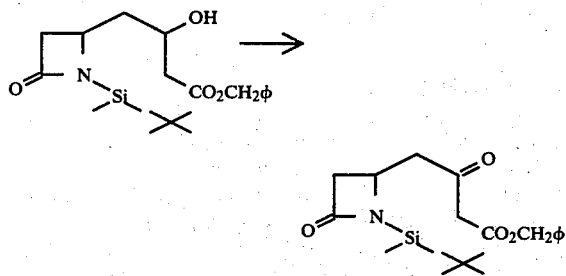

Anhydrous CrO₃ (2.274 g, 22.74 mmol) is added to a solution of anhydrous pyridine (3.597 g, 45.48 mmol) in anhydrous CH₂Cl₂ (60 ml). After stirring at room temperature (25° C.) for 15 mins, the reaction mixture is treated all at once with a solution of N-(t-butyldimethylsilyl)-4-(3-benzyloxycarbonyl-2-hydroxypropyl)-azetidin-2-one (1.432 g, 3.79 mmol) in anhydrous CH₂Cl₂ (25 ml). The resulting mixture is stirred at 25° C. for 5 mins. The CH₂Cl₂ layer is decanted from the dark, gummy residue which is triturated with more CH₂Cl₂. The combined CH₂Cl₂ phase is evaporated i.v. The residue is triturated with diethylether (Et₂O) (100 ml) in several portions and the Et₂O extracts are filtered to remove chromium salts. The ethereal filtrate is washed with 5% NaHCO₃, 1 N HCl, 5% NaHCO₃ and brine, dried with MgSO₄, filtered, and evaporated i.v. to yield N-(t-butyldimethylsilyl)-4-(3-benzyloxycarbonyl-2-oxopropyl)-azetidin-2-one (1.042 g) as a pale yellow oil: ir (neat) 5.72 (3 poorly resolved peaks), 7.59 7.98, 8.42, and 11.93 cm⁻¹;

nmr (CDCl₃) δ0.18 (s, 3), 0.22 (s, 3), 0.97 (s, 9), 2.53 (dd, 1), 2.63 (dd, 1), 3.13 (dd, 1), 3.28 (dd, 1), 3.47 (s, 2), 3.88 (m, 1), 5.17 (s, 2), and 7.33 (s, 5); mass spectrum m/e 360, 318, and 2.76.

EXAMPLE 7

Preparation of
4-(3-Benzyloxycarbonyl-2-oxopropyl)-azetidin-2-one

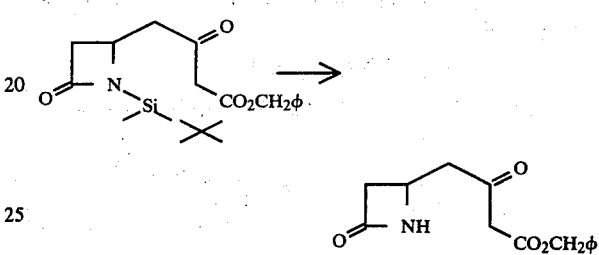

N-(t-butyldimethylsilyl)-4-(3-benzyloxycarbonyl-2-oxopropyl)-azetidin-2-one (302 mg, 0.80 mmol) is dissolved in acetic acid (4.0 ml) and the solution is diluted with H₂O (2.0 ml). The resulting solution is stirred in a securely stoppered, 10 ml, round-bottom flask in an oil bath maintained at 73° C. for 7 hrs. After cooling to room temperature, the reaction mixture is diluted with EtOAc and toluene and evaporated i.v. The residue is stripped twice with toluene to yield a yellow oil (220 mg). The crude product is chromatographed on Baker silica gel (8.8 g, packed under EtOAc). The column is eluted with EtOAc; 3 ml fractions being collected every 2.25 mins. Fractions 14–30 are combined and evaporated i.v. to provide 4-(3-benzyloxycarbonyl-2-oxopropyl)-azetidin-2-one (114 mg) as a clear oil: ir (neat) 3.04, 5.68, 5.72 and 5.83 cm⁻¹; nmr (CDCl₃) δ2.52 (ddd, 1), 2.67 (dd, 1), 3.02 (dd, 1), 3.12 (ddd, 1), 3.48 (s, 2), 3.88 (m, 1), 5.18 (s, 2), 6.17 (m, 1), and 7.37 (s, 5); mass spectrum m/e 261 (M+), 233, 219, 192, 127 and 91.

EXAMPLE 8

Preparation of
4-(3-Benzyloxycarbonyl-3-diazo-2-oxopropyl)-azetidin-2-one

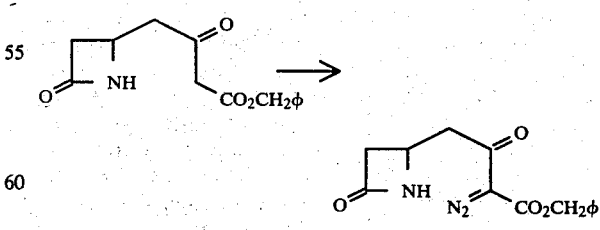

Freshly recrystallized p-carboxy benzene sulfonylazide (241 mg, 1.06 mmol) is added to a solution of 4-(3-benzyloxycarbonyl-2-oxopropyl)-azetidin-2-one (276 mg, 1.06 mmol) in anhydrous acetonitrile (6.6 ml). The resulting suspension is cooled in an ice-bath and stirred while Et₃N (443 μl, 3.18 mmol) is added. The resulting yellow solution is stirred at room temperature. A precipitate forms quickly. After 90 mins, the mixture is diluted with EtOAc (50 ml) and filtered. The filtrate is washed with H2O (2×10 ml), 0.5 N NaOH (2×10 ml), H2O (4×10 ml) and brine, dried with MgSO4, filtered, and evaporated i.v. to an off-white solid (273 mg). This is triturated with Et2O to provide 4-(3-benzyloxycarbonyl-3-diazo-2-oxopropyl)-azetidin-2-one (227 mg) as a cream colored powder: ir (film from CHCl3) 3.0, 4.65, 5.66, 5.82, 6.05, 7.21, 7.70 and 8.23 cm$^{-1}$; nmr (CDCl3) δ2.63 (ddd, 1), 2.97 (dd, 1), 3.15 (ddd, 1), 3.40 (dd, 1), 3.98 (m, 1), 5.27 (s, 2), 6.13 (m, 1), and 7.38 (s, 5); mass spectrum m/e 259, 245, 231, and 218.

EXAMPLE 9

Preparation of Benzyl 1-azabicyclo[3.2.0]heptan-3,7-dione-2-carboxylate

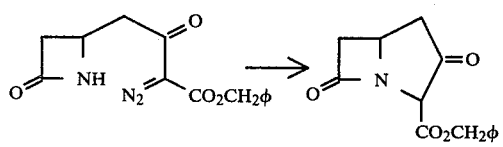

A solution of 4-(3-benzyloxycarbonyl-3-diazo-2-oxopropyl)azetidin-2-one (20 mg) in anhydrous benzene (5 ml) is irradiated for 60 mins at room temperature using a Hanovia 450 W medium-pressure mercury lamp and a Pyrex filter. Dry N2 is bubbled through the solution prior to and during the photolysis. Evaporation of the solvent in vacuo gives an oil (17 mg) which is purified by chromatography on a 250μ×20×20 cm silica gel GF plate using 3:1 φH-EtOAc as developing solvent. The band at Rf 0.3 is removed and eluted with EtOAc to give a clear oil (2.4 mg). This material is further purified by tlc on a 250μ×7.5×8.5 cm silica gel GF plate. The cleanly resolved band at Rf 0.29 is removed and eluted with EtOAc to give benzyl 1-azabicyclo[3.2.0]heptan-3,7-dione-2-carboxylate (0.7 mg) as a clear oil: ir (CCl4) 1783, 1773, and 1744 cm$^{-1}$; ir (CHCl3) 1767, 1741 cm$^{-1}$; uv (Cy) 215 nm; nmr (CDCl3) δ 2.36 (dd, J=8 and 18.5, 1), 2.90 (dd, J=6 and 18.5, 1), 2.92 (dd, J=2 and 16, 1), 3.63(dd, J=5 and 16, 1), 4.11 (m, 1), 4.71 (s, 1), 5.19 (s, 2) and 7.33 (s, 5); mass spectrum m/e 259 (M+), 231 (M+ −28), 217 (M+ −42), 203, 187, 186, 168 (M+ −91), 124, and 91; high resolution mass spectrum m/e 259.0842 (C14H13NO4).

EXAMPLE 10

Preparation of Benzyl 3-chloro-1-azabicyclo[3.2.0]hept-2-en-7-one-2-carboxylate

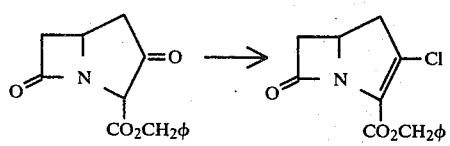

Benzyl 1-azabicyclo[3.2.0]heptane-3,7-dione-2-carboxylate (26 mg, 0.1 mmol) in anhydrous DMF (0.5 ml) containing PCl3 (27 mg, 0.2 mmol) is kept at 25° C. for 5 hrs. The mixture is diluted with toluene(5 ml), washed with H2O (5×1 ml), 5% HCl (2 ml), 5% NaHCO3 (2 ml) and brine, dried with MgSO4, and filtered. Evaporation of the solvent in vacuo provides crude benzyl 3-chloro-1-azabicyclo[3.2.0]hept-2-en-7-one-2carboxylate.

EXAMPLE 11

Preparation of Benzyl 3-bromo-1-azabicyclo[3.2.0]hept-2-en-7-one-2-carboxylate

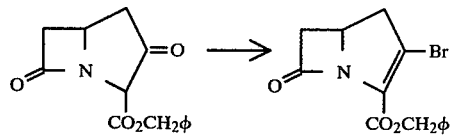

By substituting PBr3 (54 mg) for PCl3 in the preceeding example, benzyl 3-bromo-1-azabicyclo[3.2.0]-hept-2-en-7-one-2-carboxylate is obtained.

EXAMPLE 12

Preparation of Sodium 3-chloro-1-azabicyclo[3.2.0]hept-2-en-7-one-2-carboxylate

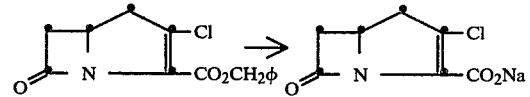

Benzyl 3-chloro-1azabicyclo[3.2.0]hept-2-en-7-one-2-carboxylate (28 mg) in methanol (2.5 ml) and water (0.5 ml) containing sodium bicarbonate (8.5 ml) is hydrogenated with 10% palladium on powdered charcoal (30 mg) at 40 psi for 30 minutes. The mixture is filtered and the catalyst is washed with water (5 ml). The combined filtrate is concentrated in vacuo to ½ its volume, washed with ethylacetate, and lyophilized to provide sodium 3-chloro-1-azabicyclo[3.2.0]hept-2-en-7-one-2-carboxylate.

EXAMPLE 13

Preparation of Sodium 3-bromo-1-azabicyclo[3.2.0]hept-2-en-7-one-2-carboxylate

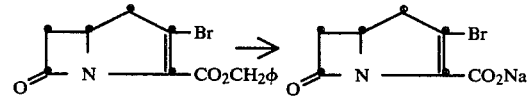

Benzyl 3-bromo-1-azabicyclo[3.2.0]hept-2-en-7-one-2-carboxylate is hydrogenolized as described in Example 12 to provide sodium 3-bromo-1-azabicyclo[3.2.0-]hept-2-en-7-one-2-carboxylate.

EXAMPLE 14

Preparation of the Benzhydrylamine salt of 3-chloro-1-azabicyclo[3.2.0]hept-2-en-7-one-2-carboxylic acid

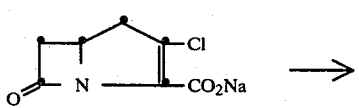

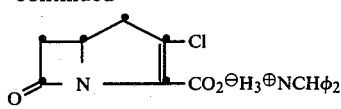

A solution of sodium 3-chloro-1-azabicyclo[3.2.0]hept-2-en-8-one-2-carboxylate (20 mg) in water (1 ml) is layered with ethyl acetate (1 ml) and stirred rapidly in an ice-bath. The pH of the mixture is brought to 2.5 with 0.1 N hydrochloride acid. The phases are separated and the aqueous portion is extracted with more ethyl acetate (2×0.5 ml). The combined ethyl acetate solution, which contains 3-chloro-1-azabicyclo[3.2.0]hept-2-en-7-one-2-carboxylic acid, is washed with brine, dried with sodium sulfate, and filtered. To the filtrate is added a solution of benzhydrylamine (19 mg) in ethyl acetate (0.5 ml). The precipitate of the benzhydrylamine salt is collected, washed with ethyl acetate, and dried in vacuo.

EXAMPLE 15

Preparation of p-(t-butyl)benzyl 3-chloro-1-azabicyclo[3.2.0]hept-2-en-7-one-2-carboxylate

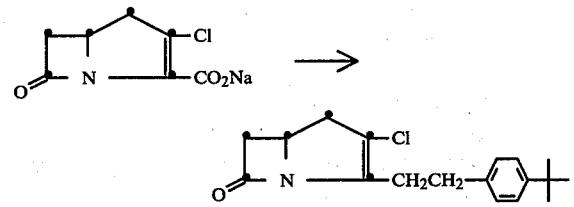

A mixture of sodium 3-chloro-1-azabicyclo[3.2.0]hept-2-en-7-one-2-carboxylate (20 mg), p-(t-butyl)benzyl bromide (34 mg), and anhydrous hexamethylphosphoramide (0.4 ml) is stirred under a nitrogen atmosphere at room temperature for 2.5 hrs. The mixture is diluted with toluene (5 ml), washed with water (5×2 ml) and brine, dried with MgSO$_4$, filtered, and concentrated in vacuo. Chromatography of the residue on a silica gel plate yields p-(t-butyl)benzyl 3-chloro-1-azabicyclo[3.2.0]hept-2-en-7-one-2-carboxylate.

EXAMPLE 16

Benzyl 1-Azabicyclo[3.2.0]Heptan-3,7-Dione-2-Carboxylate

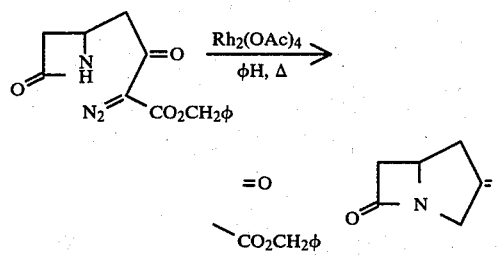

A mixture of 4-(3-benzyloxycarbonyl-3-diazo-2-oxopropyl)-azetidin-2-one (718 mg. 2.5 mMol), rhodium (II) acetate (5 mg) and anhydrous benzene (50 ml) is deoxygenated by bubbling nitrogen through it for 45 minutes. The mixture is then stirred and heated in an oil bath maintained at 80° C. for 70 minutes. After cooling to room temperature, the mixture is filtered and the filtrate is evaporated under vacuum to an oil. Crystallization from ethyl acetate (5 ml)-diethylether (20 ml) provides benzyl 1-azabicyclo[3.2.0]heptan-3,7-dione-2-carboxylate (502 mg, 77% yield) as small, white prisms: mp 100°-102°; IR (CH$_2$Cl$_2$) 1770; 1741 cm$^{-1}$; UV (dioxane) 220 nm; NMR (CDCl$_3$, 300 MHz) $\alpha$2.43 (dd,1,J=8 and 19, H4a), 2.94 (dd,1,J=6.5 and 19, H4b), 2.99 (dd,1,J=2 and 16, H6B), 3.63 (dd,1,J=5 and 16, H6$\alpha$), 4.18 (m,1,H5), 4.76 (S,1,H2), 5.23 (S,2,CH$_2\phi$), and 7.40 (S,5,ArH); MS m/e 259 (M+), 231 (M+ −28), 217 (M+ −42), 203, 187, 186, 168 (M+ −91), 124, and 91.

Anal. Calculated for C$_{14}$H$_{13}$NO$_4$: C, 64.86; H, 5.05; N, 5.40. Found: C, 64.92; H, 5.01; N, 5.11.

EXAMPLE 17

Dicyclohexylammonium 1-Azabicyclo[3.2.0]Heptan-3,7-Dione-2-Carboxylate

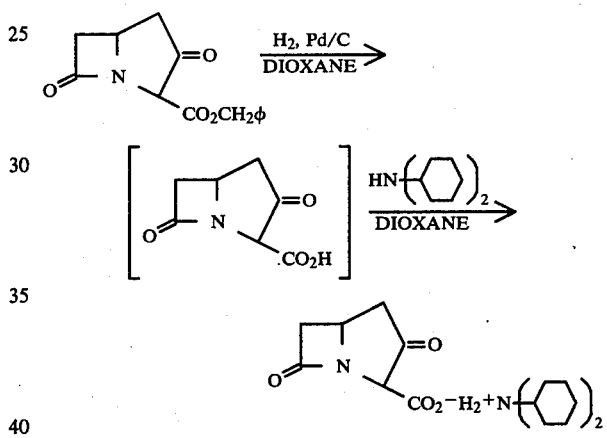

A solution of benzyl 1-azabicyclo[3.2.0]heptan3,7-dione-2-carboxylate (25.9 mg, 0.1 mMol) in dioxane (1.5 ml) is added to a mixture of 10% palladium on charcoal (5 mg) and dioxane (1.0 ml) which had been equilibrated under an atmosphere of hydrogen for 10 minutes. The resulting mixture is stirred under 1 atmosphere of hydrogen at room temperature for 30 mins., during which time 2.6 ml of hydrogen are absorbed. The mixture is filtered and the catalyst is washed with more dioxane (0.5 ml). The filtrate, which contains 1-azabicyclo[3.2.0]heptan-3,7-dione-2-carboxylic acid, is divided into two equal 1.5 ml portions.

One portion of the dioxane filtrate is treated with a solution of dicyclohexylamine (9.1 mg, 0.05 mMol) in dioxane. The solvent is removed under vacuum and the residue is triturated with diethyl ether to yield dicyclohexylammonium 1-azabicyclo[3.2.0]heptan-3,7-dione-2-carboxylate as a white powder: IR (Nujol) 1764, 1637 cm$^{-1}$; NMR (D$_2$O) $\alpha$1.1–2.2 (m,—CH$_2$CH$_2$CH$_2$CH$_2$CH$_2$—), 2.64 (dd,J=7.8 and 19.0, H4a), 2.89 (dd, J=7.9 and 19.0, H4b), 3.08 (dd, J=2 and 16.6, H6$\beta$), 3.26 (m, N—CH), 3.61 (dd, J=4.7 and 16.6, H6$\alpha$), 4.17 (m, H5), and 4.8 (br s, HOD, obscures H2 resonance).

EXAMPLE 18

Benzyl 3-(p-toluenesulfonyloxy)-1-azabicyclo[3.2.0]hept-2-2n-7-one-2-carboxylate

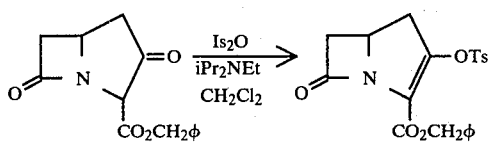

p-Toluenesulfonic anhydride (326 mg, 1 mμol) and N,N-diisopropylethylamine (192 μl, 1.1 mμol) are added to an ice-cold, stirring solution of benzyl 1-azabicyclo[2.3.0]heptan-3,7-dione-2-carboxylate (259 mg, 1 mμol) in anhydrous methylene chloride (10 ml). The resulting solution is stirred in the cold and under a nitrogen atmosphere for 2.5 hours. The solution is diluted with methylene chloride (20 ml), washed with water (10 ml). 1 M pH3 phosphate buffer (10 ml) and 5% aqueous sodium bicarbonate (2×10 ml) dried with magnesium sulfate, filtered, and evaporated under vacuum to a semi-solid. This material is triturated with ice-cold ethyl acetate (2×2 ml) and diethyl ether (2×5 ml) to provide benzyl 3-(p-toluenesulfonyloxy)-1-azabicyclo[3.2.0]hept-2-en-7-one-2-carboxylate (276 mg, 67%) as a white powder. Recrystallization from methylene chloridediethyl ether gives analytically pure product as small white needles: mp 103°–105°; IR (CH$_2$Cl$_2$) 1786, 1723, 1382, and 1190 cm$^{-1}$; NMR (CDCl$_3$) δ 2.44 (s, 3, ArCh$_3$) 3.03 (dd,1,J=3.0 and 17.0,HGβ), 3.16 (dd,1,J=8.5 and 18.7,H4a), 3.32 (dd,1,J=10.0 and 18.7,H46), 3.55 (dd,1,J=5.5 and 17.0, HG), 4.21 (m,1,H5), 5.14 (ABq,2,J=12,CH$_2$Ar), 7.35 (S,5, ArHO, 7.26 and 7.75 (two d's,4,J=9,ArH); UV(dioxane) 283 (E6600) and 277 (E6500) nm.

Anal., Calculated for C$_{21}$H$_{19}$NO$_6$S: C, 61.01; H, 4.63; N, 3.39. Found: C, 59.94; H, 4.47; N, 3.26.

EXAMPLE 19

Benzyl 3-(p-nitrobenzenesulfonyloxy)-1-azabicyclo[3.2.0]hept-2-en-7-one-2-carboxylate

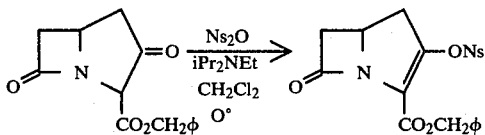

An ice-cold solution of benzyl 1-azabicyclo[3.2.0]heptan-3,7-dione-2-carboxylate (20 mg, 0.077 mmol) in methylene chloride (2 ml) is treated with p-nitrobenzenesulfonic anhydride (37.3 mg, 0.096 mmol) and N,N-diisopropylethylamine (18.3 μl, 0.015 mmol). After stirring in the cold for 20 minutes, the solution is diluted with cold methylene chloride (1 ml) and cold 0.1 M pH 7 phosphate buffer (2 ml) and shaken. The organic phase is separated, washed with cold 0.1 M pH 7 phosphate buffer (2×2 ml), water and brine, dried with magnesium sulfate, and filtered. The filtrate is diluted with cold methanol (0.5 ml) and quickly evaporated under vacuum to give a solid. The crude product is triturated with cold methanol and dried under vacuum to provide benzyl 3-(p-nitrobenzenesulfonyloxy)-1-azabicyclo[3.2.0]hept-2-en-7-one-2-carboxylate (26 mg) as a white solid: mp 86°–88°; IR (CH$_2$Cl$_2$) 1794, 1723, 1521, and 1344 cm$^{-1}$; UV (CHCl$_3$) 257 (ε 10,600) and 280 (ε 7,600) nm; NMR (CDCl$_3$) ε 3.08 (dd, 1, J=3.6 and 17, H6β), 3.25 (dd, 1, J=8.8 and 18, H3a), 3.35 (dd, 1, J=9.8 and 18, H4b), 3.59 (dd, 1, J=5.4 and 17, H6α), 4.26(m,1,H5), 5.10 (ABq, 2, J=21.2, CH$_2$φ), 7.32 (s, 5, C$_6$H$_5$), 8.03 and 8.22 (two d's, 4, J=9.3, NO$_2$C$_6$H$_4$).

Preparation of p-nitrobenzene sulfonic anhydride

A mixture of p-nitrobenzenesulfonic acid (20 g), phosphorous pentoxide (50 g) and 1,2-dichloroethylene (100 ml) is heated at reflux for 4 days. The hot supernatant is decanted from the gummy residue and allowed to cool to room temperature. The resulting crystalline precipitate of p-nitrobenzenesulfonic anhydride (1.5 g) is collected, washed with anhydrous diethylether, and dried under vacuum. The gummy residue is twice more refluxed overnight with 100 ml portions of dichloroethylene and worked up as above to provide additional p-nitrobenzenesulfonic anhydride (4.0 g): mp 171°–172°.

EXAMPLE 20

Benzyl 3-Diphenylphosphoryl-1-Azabicyclo[3.2.0]Hept-2-En-7-One-2-Carboxylate

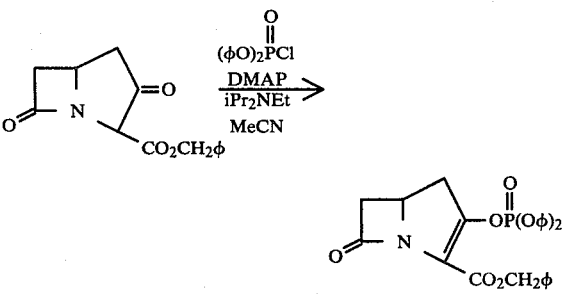

An ice-cold, stirring solution of benzyl 1-azabicyclo[3.2.0]heptan-3,7-dione-2-carboxylate (13 mg, 0.05 mMol), 4-dimethylamine pyridine (1.2 mg, 0.01 mMol) and N,N-diisopropylethylamine (12.2 μl, 0.07 mMol) in anhydrous acetonitrile (0.5 ml) is treated with diphenyl chlorophosphate (12.4 μl, 0.06 mMol). The resulting solution is stirred in the cold and under a nitrogen atmosphere for 2 hours, then diluted with methylene chloride (5 ml), washed with water (2 ml), 0.1 M pH 7 phosphate buffer (2 ml) and brine, dried over magnesium sulfate, and filtered. Evaporation of the filtrate under vacuum leaves crude benzyl 3-diphenylphosphoryl-1-azabicyclo[3.2.0]-hept-2-en-7-one-2-carboxylate (22 mg) as an oil: UV (dioxane) 281 nm; NMR(CDCl$_3$) α 2.90 (dd,1,J=3 and 17, H6β), 317(m,2,H4a and H4b), 3.52 (dd,1,J=5.5 and 17, H6α), 4.13 (m,1,H5), 5.28(S,2,CH$_2$φ), and 7.30(m,15,ArH).

EXAMPLE 21

N-(t-Butyldimethylsilyl)-4-[3-(p-nitrobenzyloxycarbonyl)-2-hydroxypropyl]-azetidin-2-one

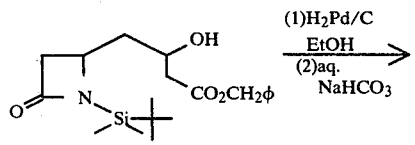

-continued

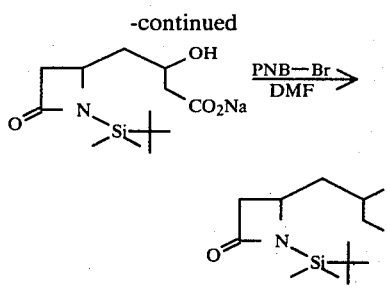

A mixture of crude N-(t-butyldimethylsilyl)-4-(3-benzyloxycarbonyl-2-hydroxypropyl)-azetidin-2-one (11.33 g, 30 mmol), ethanol (300 ml) and 10% palladium on charcoal (1.13 g) is hydrogenated at 50 psi for 1 hour. The mixture is filtered and the filtrate is treated with water (150 ml) containing sodium bicarbonate (2.52 g, 30 mmol) and concentrated under vacuum to ca 100 ml. The aqueous concentrate is washed with ethyl acetate (2×100 ml) and lyophilized to provide the sodium carboxylate (7.70 g) as a white powder.

The sodium salt and p-nitrobenzyl bromide (6.48 g, 30 mmol) are dissolved in anhydrous dimethyl formamide (150 ml) under a nitrogen atmosphere. After standing for 1 hour at room temperature, the solution is evaporated under vacuum to a semi-solid. The residue is taken up in ethyl acetate (200 ml), washed with water (2×200 ml) and brine, dried over magnesium sulfate, filtered, and evaporated under vacuum. The residual yellow oil is chromatographed on silica gel (250 g) using 1:1 toluene-ethyl acetate as eluting solvent to provide N-(t-butyldimethylsilyl)-4-[3-(p-nitrobenzyloxycarbonyl)-2-hydroxypropyl]-azetidin-2-one (8.92 g, 70%) as an oil which solidified on standing: IR (CH$_2$Cl$_2$) 3585, 1733, 1527, and 1350 cm$^{-1}$; NMR (CDCl$_3$) δ 0.22 (s,3,CH$_3$), 0.25 (s,3,CH$_3$), 0.93 (s,9,C(CH$_3$)$_3$), 1.16–2.33 (m,2,CH—C$\underline{H}_2$—CH), 2.40–3.47 (m,3,OH and H3 and H3β), 2.55 (d,2,J=6, CH$_2$CO$_2$), 3.50–4.33 (m,2,H4 and CH—OH), 5.30 (s,2,CH$_2$Ar), and 7.55, 8.27 (two d's,4,J=8.5, ArH).

EXAMPLE 22

N-(t-Butyldimethylsilyl)-4-[3-(p-nitrobenzyloxycarbony)-2-hydroxypropyl]-azetidin-2-one

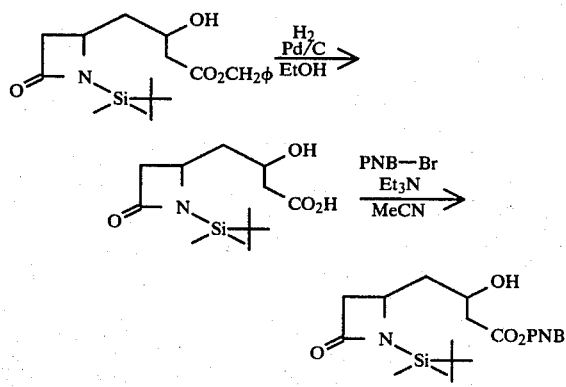

A mixture of crude N-(t-butyldimethylsilyl)-4-(3-benzyloxycarbonyl-2-Hydroxypropyl)-azetidin-2-one (13.46 g, 35.6 mmol), 10% palladium on charcoa, and ethanol (200 ml) is hydrogenated at 40 psi for 30 mins. The mixture is filtered and the filtrate is evaporated under vacuum and stripped with toluene to give N-(t-butyldimethylsilyl)-4-(3-carboxy-2-hydroxypropyl)-azetidin-2-one (9.51 g) as an off-white solid: IR (neat film from Me$_2$CO) 3200 (br), 1735, and 1700 (shifts to 1590 with Et$_3$N) cm$^{-1}$; NMR (Me$_2$CO—d$_6$) δ 0.25 (s,6,2CH$_3$), 0.98 (s,9,C(CH$_3$)$_3$) 1.17–2.33 (m,2,CH—C C$\underline{H}_2$—CH), 2.50 (d,2,J=6.5, CH$_2$CO$_2$), 2.50–3.40 (m,2,H3 and H3β), 3.97 (m,2,H4 and C$\underline{H}$OH); MS on bistrimethylsilyl derivative m/e 431 (M+), 416(M+ −57) and 332 (374-42).

The crude carboxylic acid is suspended in anhydrous acetonitrite (150 ml) and treated with p-nitrobenzyl bromide (7.56 g, 35 mμol) and triethylamine (4.9 ml, 35 mμol). The resulting solution is kept at room temperature for 2 days and then in a refrigerator for 3 days. The reddish orange solution is evaporated under vacuum and the residue shaken with ethyl acetate (100 ml, 2×50 ml) and filtered to remove triethylammonium bromide. The ethyl acetate filtrate is washed with water (3×100 ml) and brine, dried with magnesium sulfate, filtered, and evaporated under vacuum to an amber oil (13.62 g). Crystallization from diethyl ether affords N-(t-butyldimethylsilyl)-4-[3-(p-nitrobenzyloxycarbonyl)-2-hydroxypropyl]azetidin-2-one (6.84 g) as an off-white powder. Chromatography of the mother liquors on a silica gel column using 1:1 toluene-ethyl acetate as eluting solvent affords addition product (3.14 g) as an oil which solidifies.

EXAMPLE 23

N-(t-Butyldimethylsilyl)-4-[3-(p-nitrobenzyloxycarbonyl)-2-oxopropyl]-azetidin-2-one

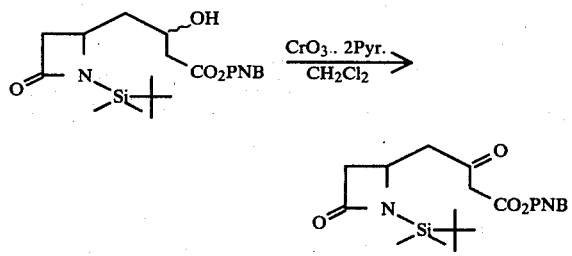

Anhydrous chromium trioxide (16.88 g 169 mmol) is added to a solution of anhydrous pyridine (27.3 ml, 338 mmol) in anhydrous methylene chloride (470 ml). The resulting mixture is stirred at room temperature for 30 minutes and then treated with a solution of N-(t-butyldimethylsilyl)-4-[3-(p-nitrobenzyloxycarbonyl)-2-hydroxypropyl]-azetidin-2-o one (8.92 g, 21.1 mmol) in methylene chloride (80 ml). The reaction mixture is stirred an additional 15 minutes at room temperature and then treated with 2-propanol (6.75 ml). The methylene chloride phase is decanted from the dark, tary residue and evaporated under vacuum. The residue from this operation is triturated with diethyl ether (350 ml) and filtered through a pad of magnesium sulfate which is washed with additional ether (150 ml). The ethereal filtrate is washed with water (200 ml), 5% aqueous sodium bicarbonate (200 ml) and brine, dried with magnesium sulfate, filtered, evaporated under vacuum, and stripped with toluene to afford the crude product (5.99 g) as an amber oil. Chromatigraphy on a silica gel column using 3:2 petroleum etherethyl acetate as eluting solvent yields N-(t-butyldimethylsilyl)-4-[3-(p-nitrobenzyloxycarbonyl)-2-oxopropyl]-azetidin- 2-one (5.17 g, 58%) as a pale yellow, viscous oil which solidifies. Trituration with diethyl ether gives the product as small, white crystals: mp 65°–66.5°, IR (CH$_2$CL$_2$) 1732, 1522, and 1350 cm) NMR (CDCl$_3$) δ 0.20 (s,3,CH$_3$), 0.23 (s,3,CH$_3$), 0.93 (s,9,C(CH$_3$)$_3$), 2.58 (dd,1,J=2.7 and 15.7, H3β), 2.72 (dd,1,J=9.4 and 18.2, CH$_2$COCH$_2$CO$_2$), 3.19 (dd,1,J=4.0 and 18.2, CH$_2$COCH$_2$CO$_2$), 3.35 (dd,1,J=5.3 and 15.7,H3α), 3.55 (s,2,COCH$_2$CO$_2$), 3.90 (m,1,H4), 5.30 (s,2,CH$_2$Ar), 7.55 and 8.25 (two d$^{15}$,4,J=8.5, ArH); MS m/e 405 (M+−15), 363 (M+−57), 321 (363-42) and 136.

Anal, Calculated for C$_{20}$H$_{28}$N$_2$O$_6$Si: C,57.12; H,6.71; N,6.66. Found: C,57.28; H,6.75; N,6.60.

EXAMPLE 24
4-[3-(P-NITROBENZYLOXYCARBONYL)-2-OXO-PROPYL]AZETIDIN-2-ONE

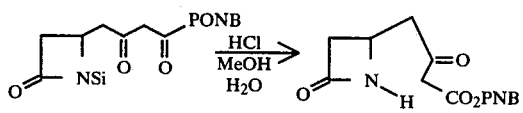

A solution of N-(t-butyldimethylsilyl)-4-[3-(p-nitrobenzyloxycarbonyl)-2-oxopropyl]-azetidin-2-one (5.17 g, 12.3 mMol) in methanol (55 ml) is treated with 1 N hydrochloric acid (6.2 ml) and then kept at room temperature for 200 mins. The solution is treated with 1 M dipotassium hydrogenphosphate (6.2 ml) and concentrated under vacuum. The residue is taken up in ethyl acetate (100 ml), washed with brine, dried over magnesium sulfate, filtered, and evaporated under vacuum. Triturating the resulting oil with diethyl ether yields 4-[3-(p-nitrobenzyloxycarbonyl)-2-oxopropyl]-azetidin-2-one (3.42 g, 91%) as an off-white powder: mp 50°–52°; IR (CH$_2$Cl$_2$) 3416, 1767, 1723, 1528, and 1352 cm$^{-1}$; NMR (CDCl$_3$) α2.60 (ddd,1,J=1,2.7, and 15.1,H3β), 2.77 (dd,1,J=8.4 and 18.2, CHCH$_2$CO), 3.13 (dd,1,J=5.1 and 18.2, CHCH$_2$CO), 3.20 (ddd,1,J=2.4, 5.0, and 15.1, H3α), 3.57 (s,2,COCH$_2$CO$_2$), 3.98 (m,1,H4); 5.27 (s,2,CH$_2$Ar), 6.28 (br s,1,NH), 7.53 and 8.23 (two d's,4,J=8.5, ArH); mass spectrum m/e 306(M+), 264(M+−42), 237, 153, 125, 111, and 136.

EXAMPLE 25
4-[3-(P-NITROBENZYLORYCARBONYL)-3-DIAZO-2-OXOPROPYL]AZETIDIN-2-ONE

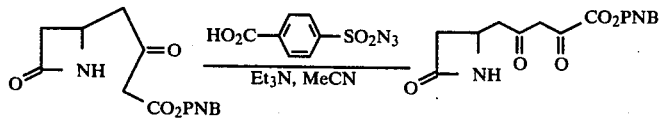

p-Carboxybenzyenesulfonylazide (2.67 g, 11.8 mMol) and triethylamine (4.68 ml, 33.6 mMol) are added to an ice-cold, stirring solution of 4-[3-(p-nitrobenzyloxycarbonyl)-2-oxopropyl]-azetidin-2-one (3.42 g, 11.2 mMol) in anhydrous acetonitrile (70 ml). The resulting mixture is stirred in the cold for 10 minutes and at room temperature for 60 minutes. The mixture is diluted with ethyl acetate (200 ml) and filtered. The filtrate is washed with water (2×100 ml), 1 M pH3 phosphate buffer (50 ml), 0.1 M pH7 phosphate buffer (100 ml), and brine, dried over magnesium sulfate, filtered, and evaporated under vacuum to a yellow foam (3.75 g). The crude product is taken up in methylene chloride (ca. 10 ml), heated briefly with activated charcoal, and filtered through a pad of magnesium sulfate. The filtrate is diluted with diethyl ether (ca. 40 ml) and scratched to yield a precipitate. The precipitate is collected, washed with ether, and dried under vacuum to provide 4-[3-(p-nitrobenzyloxycarbonyl)-3-diazo-2-oxopropyl]azetidin-2-one (3.29 g, 88%) as a pale yellow powder: mp 114.5°–116.5°; IR (CH$_2$Cl$_2$) 3413, 2142, 1767, 1724, 1657, 1530, and 1352 cm$^{-1}$; NMR (CDCl$_3$) α2.68 (ddd,1,J=1.2, 2.7, and 14.8, H3β), 3.02 (dd,1,J=8.4 and 18.0, CHCH$_2$CO), 3.22 (ddd,1,J=2.4, 4.8, and 14.8, H3α); 343 (dd,1,J=4.6 and 18.0, CHCH$_2$CO), 4.00 (m,1,H4), 5.38 (s,2,CH$_2$Ar), 6.30 (brs,1,NH), 7.57 and 8.27 (two d's,4,J=8.5, ArH); mass spectrum m/e 332(M+), 304(M+−28), 290(M+−42), 262, and 263.

Anal., calculated for C$_{14}$H$_{12}$N$_4$O$_6$: C,50.61; H,3.64; N,16.86. Found: C,50.34; H,3.42; N,16.72.

EXAMPLE 26
P-NITROBENZYL 1-AZABICYCLO[3.2.0]HEPTAN-3,7-DIONE-2-CARBOXYLATE

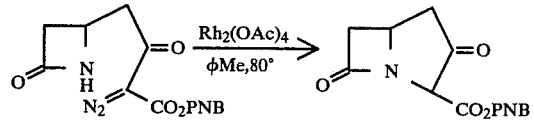

A suspension of 4-[3-(p-nitrobenzylocycarbonyl)-3-diazo-2-oxopropyl]-azetidin-2-one (2.93 g) and rhodium (II) acetate (15 mg) in anhydrous toluene (300 ml) is degassed by bubbling nitrogen through it for 60 minutes. The mixture is then stirred and heated in an oil bath maintained at 80° C. After a few minutes, the diazo compound dissolves and gas evolution commences. The mixture is heated at 80° C. for 100 minutes, then allowed to stand at room temperature for 30 mins. before filtering through a pad of celite. The filtrate is evaporated under vacuum to an oily residue which is triturated with diethyl ether to afford p-nitrobenzyl 1-azabicyclo[3.2.0]heptan-3,7-dione-2-carboxylate (2.53 g, 94%) as an off-white powder. Recrystallization from ether provides analytically pure product: mp 127°–128°: IR (CH$_2$Cl$_2$) 1776, 1753, 1529, and 1352 cm$^{-1}$; NMR (CDCl$_3$) α2.47 (dd,1,J=8.2 and 18.8 H4a), 2.98 (dd,1,J=6.8 and 18.8, H4b), 3.00 (dd,1,J=2.0 and 12.0, H6β), 3.70 (dd,1,J=4.8 and 12.0, H6α), 4.20 (m,1,H5), 4.80 (s,1,H2), 5.32 (s,2,CH$_2$Ar), 7.57 and 8.25 (two d's,4,J=8,ArH); mass spectrum m/e 304(M+), 276(M+−28), 262 (M+−42), and 168(M+−136).

Anal., calculated for C$_{14}$H$_{12}$N$_2$O$_6$: C,55.27; H,3.98; N,9.21. Found: C,55.06; H,4.03; N,8.99.

EXAMPLE 27

P-Nitrobenzyl 3-(p-Toluenesulfonyloxy)-1-azabicyclo[3.2.0]hept-2-en-7-one-2-carboxylate

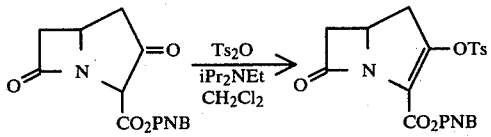

p-toluenesulfonic anhydride (520 mg, 1.59 mμol) and N,N-diisopropylethylamine (300 μl, 1.72 mμol) are added to an ice-cold, stirring solution of p-nitrobenzyl 1-azabicyclo[3.2.0]heptan-3,7-dione-2-carboxylate (484 mg, 1.59 mμol) in anhydrous methylene chloride (17 ml). The resulting solution is stirred in the cold for 2 hours, then diluted with more methylene chloride, washed with water, 1μ ph 3.4 phosphate buffer and saturated aqueous sodium bicarbonate, dried with magnesium sulfate, filtered, and evaporated under vacuum. Addition of cold ethyl acetate and a few seed crystals to the oily residue induces crystallization. The product is collected, washed with cold ethyl acetate, and dried under vacuum to afford p-nitrobenzyl 3-(p-toluenesulfonyloxy)-1-azabicyclo[3.200]hept-2-en-7-one-2-carboxylate (446 mg, 61%) as off-white crystals: mp 99°-102° (dec.); IR (neat) 1790, 1725, 1521, 1345, and 1172 cm$^{-1}$; UV (CH$_2$Cl$_2$) 272 nm; NMR (CDCl$_3$) δ 2.40 (s,3,ArCH$_3$), 3.06 (dd,1,J=3.0 and 17.2, HGβ), 3.16 (dd,1,J=9.0 and 9.0,H4a), 3.31 (dd,1,J=9.0 and 10.0, H46), 3.59 (dd,1,J=5.8 and 17.2, HG), 4.24 (m,1,H5), 5.20 and 5.32 (ABq,2,J=14.0,CH$_2$Ar), 7.32 and 7.77 (two d's,4,J=8.0, p—MeC$_6$H$_4$), 7.51 and 8.19 (two d's,4,J=8.0,p—NO$_2$C$_6$H$_4$).

EXAMPLE 28

Preparation of Pharmaceutical compositions

One such unit dosage form comprises 120 mg. of sodium 3-chloro-1-azabicyclo[3.2.0]hept-2-en-7-one-2-carboxylate with 20 mg. of lactose and 5 mg. of magnesium stearate; the resulting 145 mg mixture is placed in a No. 3 gelatin capsule. Similarly, by employing more of the active ingredient and less lactose, other dosage forms can be put up in No. 3 gelatin capsules, and, should it be necessary to mix more than 145 mg of ingredients together, larger capsules such as compressed tablets and pills can also be prepared. The following examples are illustrative of the preparation of such pharmaceutical formulations:

| TABLET | PER TABLET |
| --- | --- |
| Sodium 3-chloro-1-azabicyclo[3 . 2 . 0]-hept-2-en-7-one-2-carboxylate | 125 mg. |
| Cornstarch, U.S.P. | 6 mg. |
| Dicalcium Phosphate | 192 mg. |
| Lactose, U.S.P. | 190 mg. |

The active ingredient is blended with the dicalcium phosphate, lactose and about half of the cornstarch. The mixture is then granulated with a 15% cornstarch paste (6 mg) and rough-screened. It is dried at 45° C. and screened again through No. 16 screens. The balance of the cornstarch and the magnesium stearate is added and the mixture is compressed into tablets, approximately 0.5 inch in diameter each weighing 800 mg.

| PARENTERAL SOLUTION | |
| --- | --- |
| Ampoule: | |
| Sodium 3-chloro-1-azabicyclo[3 . 2 . 0]-hept-2-en-7-one-2-carboxylate | 500 mg. |

| OPTHALMIC SOLUTION | |
| --- | --- |
| Sodium 3-chloro-1-azabicyclo[3 . 2 . 0]-hept-2-en-7-one-2-carboxylate | 100 mg. |
| Hydroxypropylmethyl Cellulose | 5 mg. |
| Sterile Water to | 1 ml. |

| OTIC SOLUTION | |
| --- | --- |
| Sodium 3-chloro-1-azabicyclo[3 . 2. 0]-hept-2-en-7-one-2-carboxylate | 100 mg. |
| Benzalkonium chloride | 0.1 mg. |
| Sterile Water to | 1 ml. |

| TOPICAL OINTMENT | |
| --- | --- |
| Sodium 3-chloro-1-azabicyclo-8 3 . 2 . 0]-hept-2-en-7-one-2-carboxylate | 100 mg. |
| Polyethylene Glycol 4000 U.S.P. | 400 mg. |
| Polyethylene Glycol 400 U.S.P. | 1.0 gram |

What is claimed is:
1. A compound having the structure:

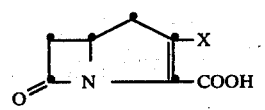

wherein X is chloro or bromo.

2. An antibacterial pharmaceutical composition comprising a therapeutically effective amount of a compound according to claim 1 and a pharmaceutical carrier therefor.

* * * * *